US012011374B2

(12) United States Patent
Smith

(10) Patent No.: US 12,011,374 B2
(45) Date of Patent: Jun. 18, 2024

(54) FOUR-BAR LINKAGE TRANSMISSION AND METHODS OF MAKING, USING, AND CONTROLLING THE SAME

(71) Applicant: Otto Bock Healthcare LP, Austin, TX (US)

(72) Inventor: Weston Smith, Brooklyn, NY (US)

(73) Assignee: Otto Bock Healthcare LP, Austin, TX (US)

( * ) Notice: Subject to any disclaimer, the term of this patent is extended or adjusted under 35 U.S.C. 154(b) by 0 days.

(21) Appl. No.: 16/726,534

(22) Filed: Dec. 24, 2019

(65) Prior Publication Data
US 2021/0186717 A1 Jun. 24, 2021

(51) Int. Cl.
A61F 2/68 (2006.01)
A61F 2/66 (2006.01)
A61H 3/00 (2006.01)
A61F 2/50 (2006.01)
A61F 2/64 (2006.01)
(Continued)

(52) U.S. Cl.
CPC .............. A61F 2/68 (2013.01); A61F 2/6607 (2013.01); A61H 3/00 (2013.01); A61F 2002/5007 (2013.01); A61F 2/644 (2013.01); A61F 2002/6614 (2013.01); A61F 2/70 (2013.01); A61F 2/74 (2021.08)

(58) Field of Classification Search
CPC ..................................................... A61F 2/6607
See application file for complete search history.

(56) References Cited

U.S. PATENT DOCUMENTS 5,181,931 A * 1/1993 van de Veen ........... A61F 2/644
623/40
5,201,776 A * 4/1993 Freeman ................. A61F 2/644
623/46
(Continued)

FOREIGN PATENT DOCUMENTS

EP 1068844 A1 1/2001
WO 2015095211 A2 6/2015

OTHER PUBLICATIONS

P.E. Nikravesh, 5.3 Graphical Velocity Analysis, Instant Center Method [retrieved on Sep. 19, 2023]. Retrieved from the Internet <URL: https://www.u.arizona.edu/~pen/ame352/Notes%20PDF/5.3%20Velocity-graphical.pdf>.*

(Continued)

Primary Examiner — Jacqueline Woznicki
(74) Attorney, Agent, or Firm — Goodwin Procter LLP

(57) ABSTRACT

Exemplary embodiments herein relate to a unique 4-bar linkage transmission provided between two adjacent links of a powered augmentation device that provides a varying mechanical advantage. Due to the kinematics of the linkage, the mechanical advantage between the actuator and the augmented joint varies with the position of the linkage. Thus, a high mechanical advantage can be provided in positions at which relatively high joint torque is required, and low mechanical advantage in positions at which relatively high joint speed is required. Consequently, the speed-torque (or velocity-force) operating area of the actuator can be consolidated by mapping the widespread output regions onto a smaller input region. This allows the actuator to be optimized for a narrower range of usage.

19 Claims, 14 Drawing Sheets

(51) Int. Cl.
  *A61F 2/70*   (2006.01)
  *A61F 2/74*   (2006.01)

(56) References Cited

U.S. PATENT DOCUMENTS

| | | | | |
|---|---|---|---|---|
| 6,632,159 | B1* | 10/2003 | Slattery | A63B 21/078 |
| | | | | 482/4 |
| 2002/0052663 | A1* | 5/2002 | Herr | F16F 9/535 |
| | | | | 623/24 |
| 2007/0198098 | A1* | 8/2007 | Roston | A61F 2/70 |
| | | | | 623/26 |
| 2013/0226048 | A1* | 8/2013 | Unluhisarcikli | A61H 1/00 |
| | | | | 601/34 |
| 2017/0290684 | A1 | 10/2017 | Lenzi et al. | |
| 2020/0397598 | A1* | 12/2020 | Okuda | A61F 2/64 |

OTHER PUBLICATIONS

"Motor Constants". Wikipedia article accessed Oct. 4, 2023. <https://en.wikipedia.org/wiki/Motor_constants>.*
European Search Report for the European Patent Application No. 20216943, dated May 27, 2021, 8 pages.

* cited by examiner

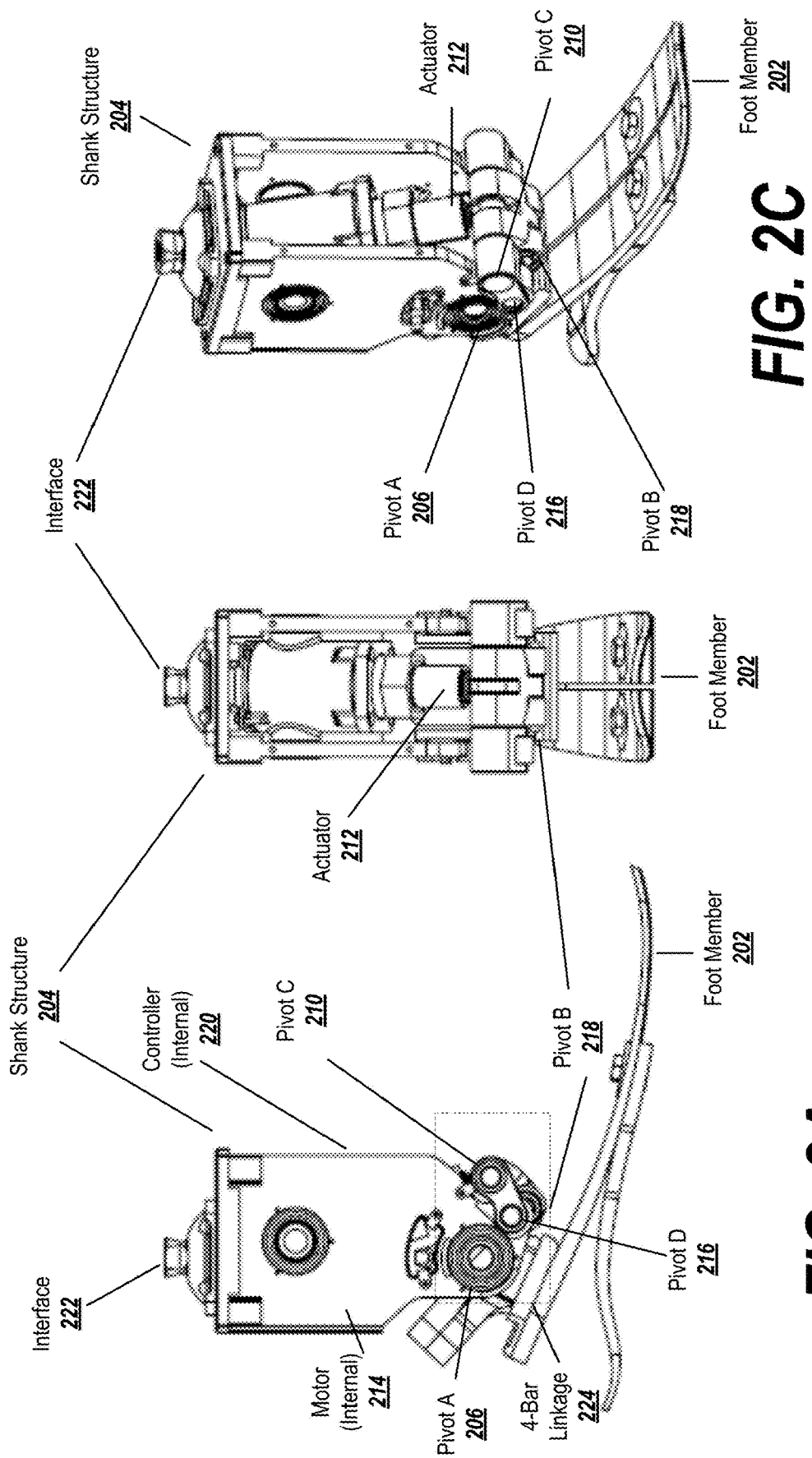

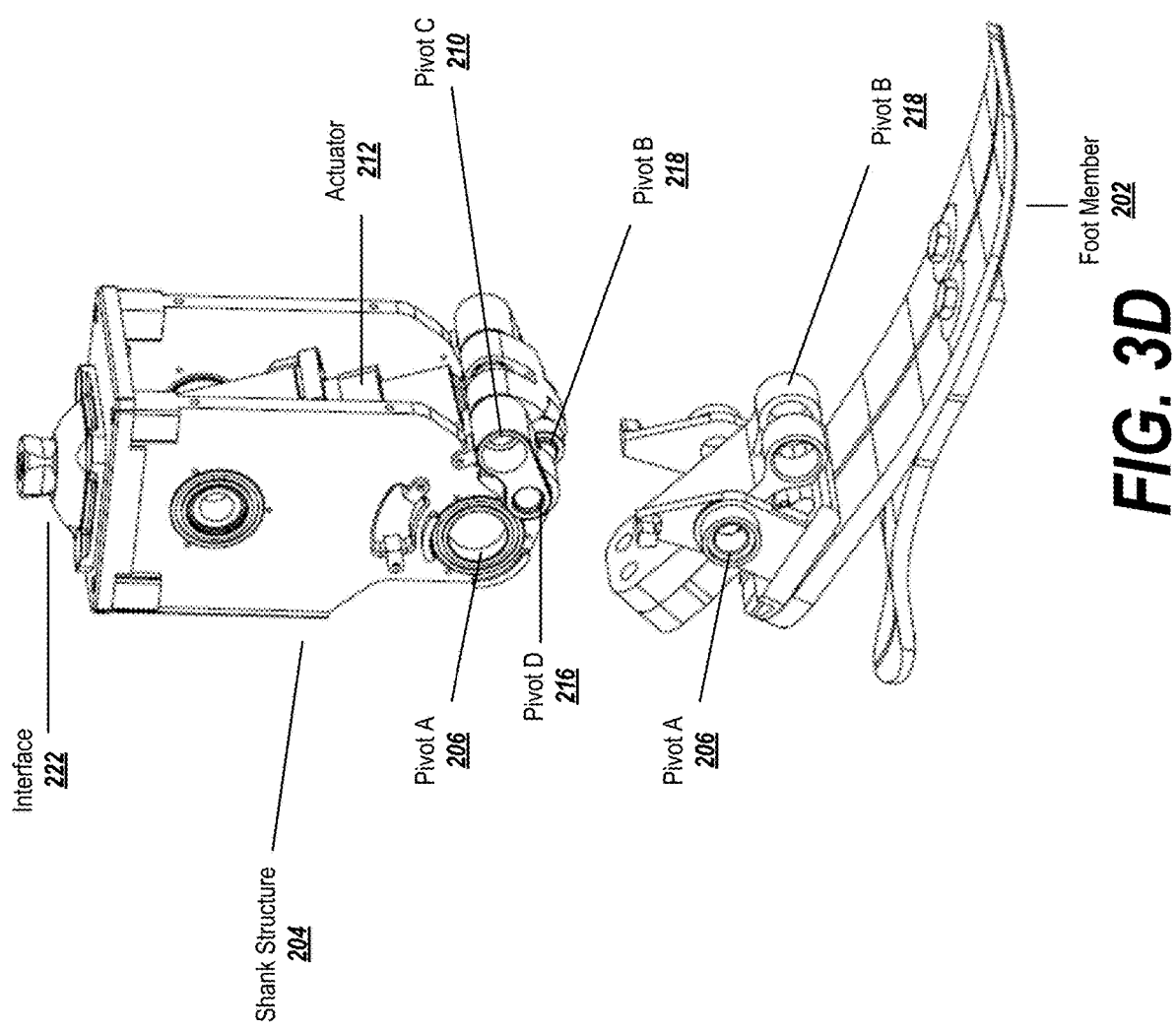

FOUR-BAR LINKAGE TRANSMISSION AND METHODS OF MAKING, USING, AND CONTROLLING THE SAME

FIELD OF THE INVENTION

The present application relates to improvements in transmissions for augmentation devices, and in particular a four-bar linkage for a transmission in a powered human prosthesis, orthosis, exoskeleton, or the like.

BACKGROUND

Powered augmentation devices may be used to replace a limb or augment its power; examples of such devices include prosthetics, orthotics, exoskeletons, etc. In a powered augmentation device, power is typically provided by an actuator, which applies force or toque at appropriate times as defined by the biomechanics of the limb being augmented or replaced or by the requirements of a task.

To take an actuated prosthetic ankle joint as one example, such joints are typically arranged with a linear actuator (e.g. a motor-driven screw) bridging the two halves of the joint. Such designs typically use a screw (usually a ball screw or lead screw) and a belt or gear transmission to an electric motor, or use hydraulic linear actuators.

One problem that arises in connection with such devices is that the actuator typically needs to be capable of operating at both high speed and high torque (albeit not simultaneously). Consequently, the actuator needs to be capable of operating over a broad range of speed-torque operating points.

By altering the transmission ratio of the belt or the screw, the peak speed could be reduced at the cost of raising the peak torque, or the peak torque could be reduced at the cost of raising the peak speed, but the speed and torque peaks cannot both be reduced.

In a conventional design, the lever arm of the actuator to the joint may change as the joint moves, providing a varying mechanical advantage. This effect may be exploited to apply a relatively high advantage where high torque is needed and low advantage where low torque is needed. However, the possibilities for shaping the mechanical advantage relative to the joint position are limited, and the mechanical advantage available from the lever arm is limited by the available space around the joint.

A broad range of operating conditions, and the design trade-off between peak speed and peak torque, is typical of powered augmentation devices, but is undesirable for the design of the actuator. The necessity of covering such a broad operating range tends to make the actuator larger, heavier, and more expensive than it would be if it were optimized for a narrower operating range. A transmission that can provide additional, varying mechanical advantage is therefore beneficial to the design of augmentation devices.

BRIEF DESCRIPTION OF THE INVENTION

Exemplary embodiments described herein relate to a unique four-bar linkage transmission for a powered augmentation device that provides a highly variable mechanical advantage. This varying mechanical advantage is designed to provide a high mechanical advantage in positions at which relatively high joint torque or low joint speed is required and low mechanical advantage in positions at which relatively low joint torque or high joint speed is required.

Such a transmission may be designed to map a relatively broad operating range at the transmission output onto a relatively narrow operating range at the transmission input (e.g. at the actuator, motor, or any other suitable transmission element). This allows the actuator to be optimized for a narrower operating range (speed and force for a linear actuator, or speed and torque for a rotary actuator). This optimization may provide a variety of benefits depending on the actuator type and design priorities, such as increasing actuator efficiency or reducing the necessary supply voltage of an electric motor. Other types of actuators (e.g., hydraulic) may be optimized for application-specific benefits. A transmission may be designed such that the peak speed and the peak torque may both be reduced from what could have been achieved with a fixed-ratio transmission element, such as a belt drive.

As an example, FIG. 1 contrasts the motor operating range of a conventional system with that of a system employing an exemplary 4-bar transmission as described herein. Line 102 represents the conventional system. Line 104 represents the system with the exemplary 4-bar transmission. As illustrated in this graph, the high speed and high torque regions of line 102 are consolidated to a much smaller area in line 104. Whereas the conventional system described by line 102 must cover a broad operating range, the exemplary system with a four-bar transmission occupies a smaller range of operating conditions, staying below approximately 11,000 RPM and 0.55 Nm. As compared with the conventional system, the exemplary system reduces both the peak motor speed and the peak motor torque. This is possible because the transmission ratio is relatively high in positions at which high torque output is required and relatively low at positions at which high speed output is required.

Consolidating the speed-torque (or velocity-force) operating range of the actuator is beneficial for optimizing the actuator itself (e.g. a motor, motor and screw, or hydraulic piston) and for optimizing the control electronics and power source (e.g. battery) that drive the actuator. For example, when the actuator is a motor, aspects of the motor may be defined by a torque constant or speed constant associated with the motor. The torque constant and/or speed constant may be selected based on the varying mechanical advantage described herein so as to tune the motor to a limited operating range (as compared to an operating range for a device without the exemplary 4-bar linkage) defined by the varying mechanical advantage.

The four-bar linkage transmission provides mechanical advantage in a compact and lightweight form, it can reduce the load carried by the actuator, and it can be designed to take input from either a rotary or a linear actuator. These features can be advantageous for reducing the bulk, weight, and cost of an augmentation device.

A typical joint in a human augmentation device consists of a proximal structure and a distal structure joined by a pivot. The pivot either replaces or coincides with an anatomical joint, and the proximal and distal structures of the augmentation device replace or coincide with the proximal and distal anatomy on either side of the anatomical joint. For example, in an elbow orthosis the pivot would coincide with the elbow joint and the proximal and distal structures of the device would attach to the upper and lower arm of the user. As another example, in an ankle-foot prosthesis, the pivot would replace the ankle joint and the proximal and distal structures of the device would replace all or part of the lower leg and foot. The proximal and distal structures of the augmentation device may comprise multiple parts and may include other pivots or flexible members.

Typically, an actuator is disposed between the proximal and distal structures such that it can create a force or torque between them, or cause them to rotate relative to each other at the pivot.

The augmentation device described herein is associated with a single anatomical joint. One of ordinary skill in the art will recognize that the invention may also apply to one or more joints of a multi-joint augmentation device, such as a walking exoskeleton or a knee-ankle-foot prosthesis.

For ease of discussion, the four pivots of the transmission are respectively referred to as pivots A, B, C, and D. The four links of the linkage are referred to by the pairs of pivots that they connect: links AB, BC, CD, and AD. The four links of the linkage are structures that connect the pivots. They may comprise multiple parts, including flexible parts, and may have other functions in addition to their function in the linkage mechanism. Link AD may correspond to a shin member of an ankle device and Link AB may correspond to a prosthetic foot.

Let Pivot A be the pivot associated with the anatomical joint, which joins the proximal and distal structures of the augmentation device and allows rotation of the proximal and distal structure about a single axis of rotation. Links AB and AD, joined by pivot A, are the proximal and distal structures of the augmentation device (for the sake of generality, it does not matter which link is proximal and which is distal). Links BC and CD, are free to move relative to the other links, subject to the kinematics of the linkage.

An actuator driving the linkage is disposed so as to apply a force or torque on one part of the linkage relative another. For example, a linear actuator may be disposed between link AD and link CD, or a rotary actuator may be disposed between links BC and CD at pivot C. Many arrangements of the actuator are possible.

The linkage transmission creates a mechanical advantage between pivot A and the actuator due to the kinematics of the links, which will depend on their arrangement in a particular design. Take link AD as a kinematic ground, such that motion of the other links are described relative to link AD. Link CD is constrained to rotate about pivot D. Link AB is constrained to rotate about pivot A. Link BC is constrained by the motions of links AB and CD, and those constraints create a virtual instantaneous center of rotation (ICR) for link BC.

Link BC can be seen as a rotary lever with its ICR as the fulcrum. This leverage creates the mechanical advantage of the linkage transmission. The ICR moves relative to link BC as the linkage moves through its range of motion, and so the transmission ratio varies.

The operation of the linkage transmission will be described in greater detail below for an exemplary embodiment, and one of ordinary skill in the art will understand that the design can be generalized to a family of four-bar transmissions with different variable transmission properties. The general description provided in the preceding paragraphs applies, for example, to the hardware depicted in FIGS. 2A-3C.

In the disclosed invention, one pivot of the four-bar linkage has the role of the anatomical joint being replaced or augmented by the device. This is in contrast to an invention disclosed by Lenzi et. Al. in US20170290684, which also employs a four-bar linkage in a powered ankle-foot prosthesis to create a position-dependent variable transmission. In US20170290684, the role of the anatomical joint is played by the instantaneous center of rotation (ICR) of the foot member relative to the shank member. The foot member and shank member are on opposed, rather than adjacent, links in the four-bar linkage, and the kinematics of the linkage create a virtual center of rotation that does not correspond to any one of the physical pivots in the linkage. The motion of the virtual joint location relative to the shank member is critical to the varying transmission ratio of that invention. In the exemplary embodiments described herein, which are also powered ankle-foot prostheses, the joint is a physical pivot of the four bar linkage, and does not move relative to either the shank member or the foot member.

BRIEF DESCRIPTION OF THE DRAWINGS

FIG. 2A depicts a side view of an exemplary prosthetic ankle employing a 4-bar linkage according to one embodiment.

FIG. 2B depicts a font view of an exemplary prosthetic ankle employing a 4-bar linkage according to one embodiment.

FIG. 2C depicts a perspective view of an exemplary prosthetic ankle employing a 4-bar linkage according to one embodiment.

FIG. 3D depicts an exploded view of an exemplary prosthetic ankle employing a 4-bar linkage according to one embodiment.

DETAILED DESCRIPTION OF EXAMPLE EMBODIMENTS

Although exemplary embodiments are generally described herein, for illustration purposes, with respect to a powered ankle joint prosthesis, one of ordinary skill in the art will recognize that the present invention is not so limited. The described four-bar linkage may also be employed in connection with other joints, such as knees, elbows, hips, etc., and may be employed in connection with other powered augmentation devices, such as orthoses, exoskeletons, etc.

Figure 1:
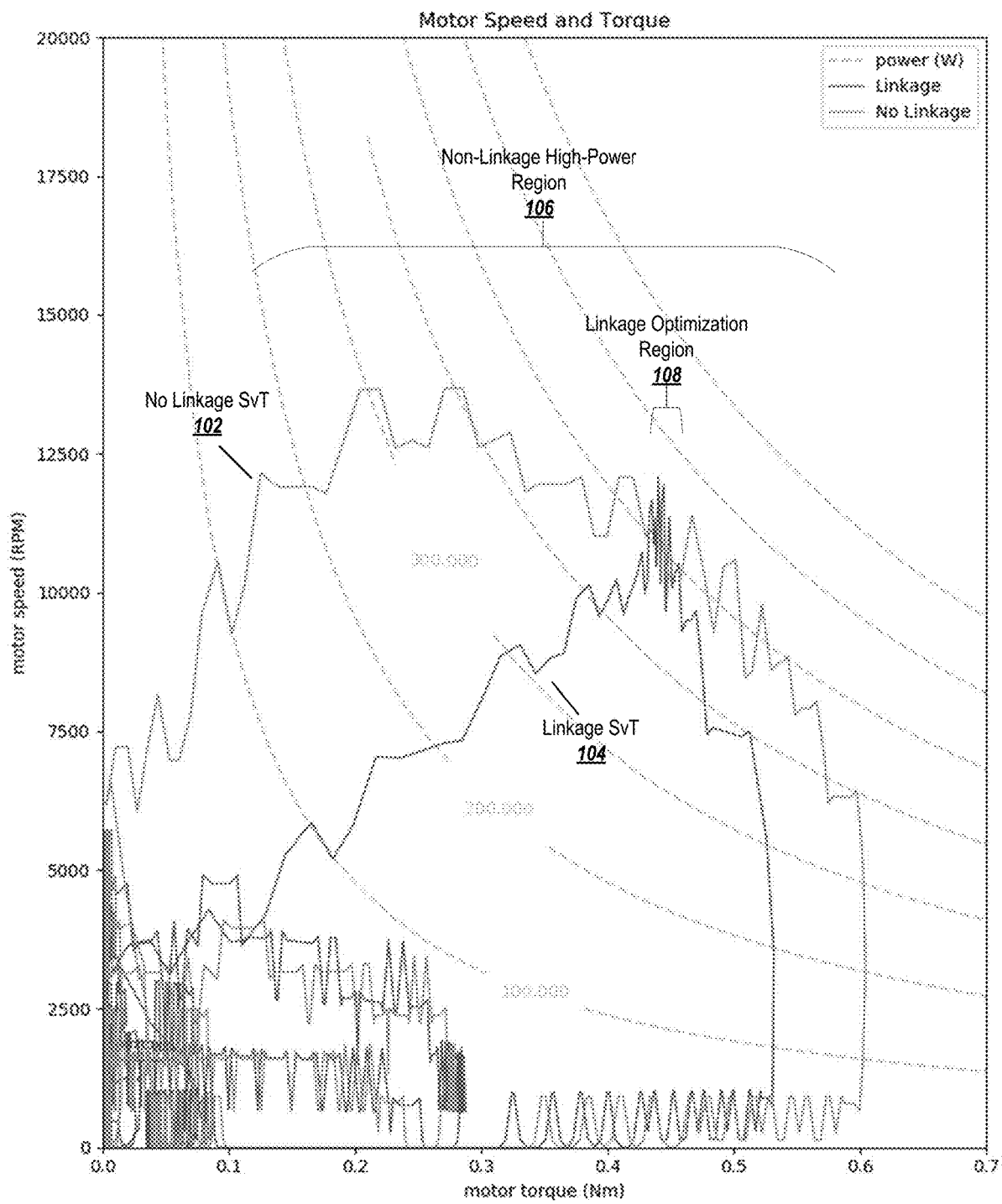
FIG. 1 depicts a graph of motor torque versus motor speed for an exemplary embodiment as compared to a no-linkage example.
Figures 3A, 3B, 3C:
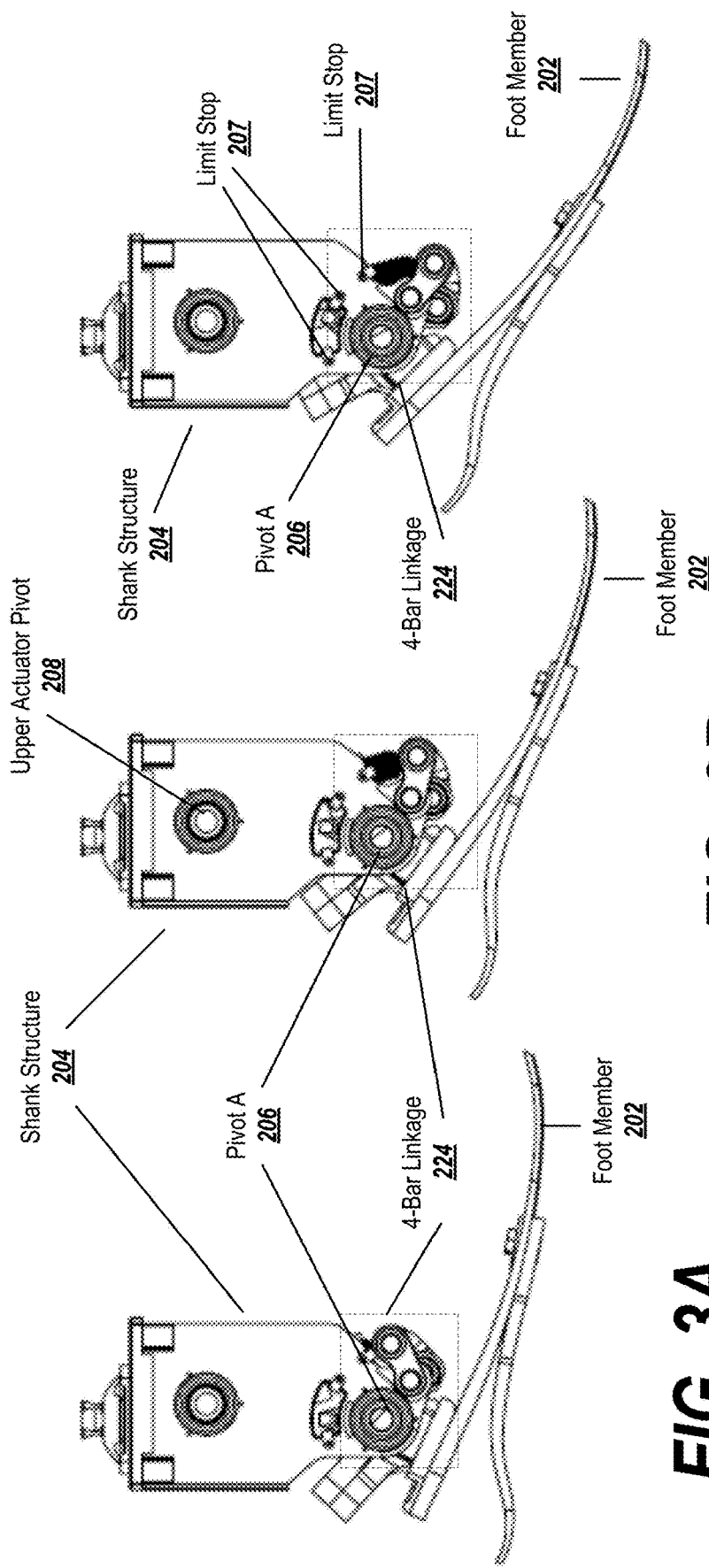
FIG. 3A depicts a side view of an exemplary prosthetic ankle employing a 4-bar linkage according to one embodiment at a first time in a gait cycle.
FIG. 3B depicts a side view of an exemplary prosthetic ankle employing a 4-bar linkage according to one embodiment at a second time in a gait cycle.
FIG. 3C depicts a side view of an exemplary prosthetic ankle employing a 4-bar linkage according to one embodiment at a third time in a gait cycle.

Turning to FIGS. 2A-2C, a first embodiment of an exemplary powered ankle-foot prosthesis employing an exemplary four-bar linkage is depicted. Broadly speaking, the ankle-foot prosthesis is provided in two pieces: a foot structure 202 and a shank structure 204, connected by an ankle joint. The ankle joint allows the foot structure 202 and shank structure 204 to rotate with respect to each other, as shown for instance in FIGS. 3A-3C. The prosthesis may connect to a socket or other connection point on a lower limb or knee prosthesis of a user through an interface 222.

Continuing the naming convention above, the linkage pivots are named A, B, C, and D, with pivot A corresponding to the ankle joint. The four links of the linkage 224 are identified based on the names of the pivots that they connect. Link AB is the foot structure 202, which is associated with the anatomical foot. Link AD is the shank structure 204, which is associated with the anatomical shank or lower leg. Link CD is a separate structure that pivots about the shank structure 204 at D. Link BC is another separate structure that rotates about the foot structure at B and connects to Link CD at pivot C.

In the described embodiment, a linear actuator 212 is disposed between an upper actuator pivot 208 on the shank structure and a lower actuator pivot that is coaxial with pivot C of the linkage. In the first embodiment the actuator may comprise a rotary electric motor and a ball screw, which converts the motor torque to linear force.

Consider the state of the linkage when a force is applied by the actuator and opposed by an external force at the foot (part of link AB), such that the mechanism is in static equilibrium. The forces throughout the linkage can be determined using free body diagrams and solving the force and torque balances for each link.

As an alternative to free body diagrams of each part of the linkage, it is possible to consider link BC as a rigid body constrained to rotate about its ICR. This approach is useful for describing the contribution of the linkage transmission to the overall transmission ratio in the exemplary embodiment.

Link BC is kinematically constrained by the adjacent links such that pivot C must revolve about pivot D and pivot B must revolve about pivot A. Since pivot C must revolve about D, the instantaneous motion is perpendicular to a line through C and D, and the ICR must lie on that line. Similarly, pivot B must revolve about A, and the ICR must be on a line through A and B. Therefore, the ICR must be at the intersection of the two lines passing through A and B and through C and D. We can model the kinematic constraint on link BC as a virtual pivot at the ICR—the link's motion is constrained to rotation about the instantaneous location of the ICR.

Figure 4A:
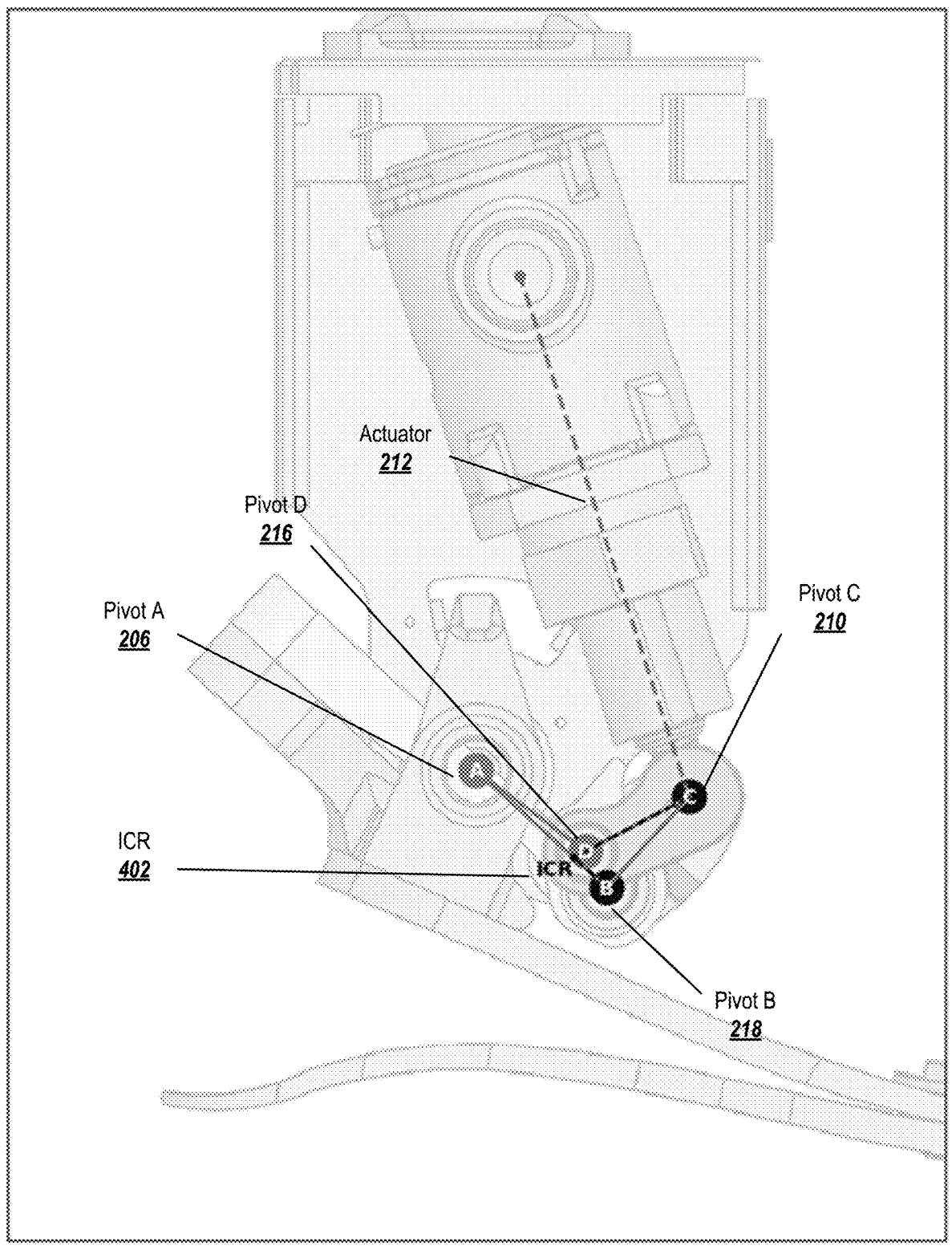
FIG. 4A depicts a side view illustrating pivot locations for an exemplary 4-bar linkage according to a first embodiment.

Referring to FIG. 4A and considering a free body diagram of link BC, the actuator force at pivot C is reacted at pivot B and at the ICR. Decompose the forces at C and B into components that are radial and circumferential to the ICR. Calculating a torque balance about the ICR gives the relation:

$Fb\_cir = Fc\_cir * (Licr\_c / Licr\_b)$, where:

Fc_cir is the circumferential force at C
Fb_cir is the circumferential force at B
Licr_c is the distance from the ICR to C
Licr_b is the distance from the ICR to B The joint torque, or torque on link AB about pivot A, resulting from the actuator force is $T\_a = La\_b * Fb\_cir = La\_b * Fc\_cir * (Licr\_c / Licr\_b)$, where La_b is the distance from pivot A to pivot B.

If we consider the four-bar transmission to have Fc_cir as input and Fb_cir as output, then the transmission ratio is (Licr_c/Licr_b). When the ICR is closer to B than to C, FcB is greater than FcC, or the output is greater than the input, providing a mechanical advantage greater than 1 to the actuator. Since the ICR moves in relation to pivots B and C during the motion of the linkage, the linkage provides a varying, position-dependent transmission ratio.

With the pivots in the positions shown in FIG. 4A, which is the fully dorsiflexed position, the ICR is at the intersection of the two dotted lines (near pivot D), which show the relative distances from the ICR to pivots C and B. The distance to C is approximately three times the distance to B, providing a transmission ration of about 3:1 in this position.

Figure 4B:
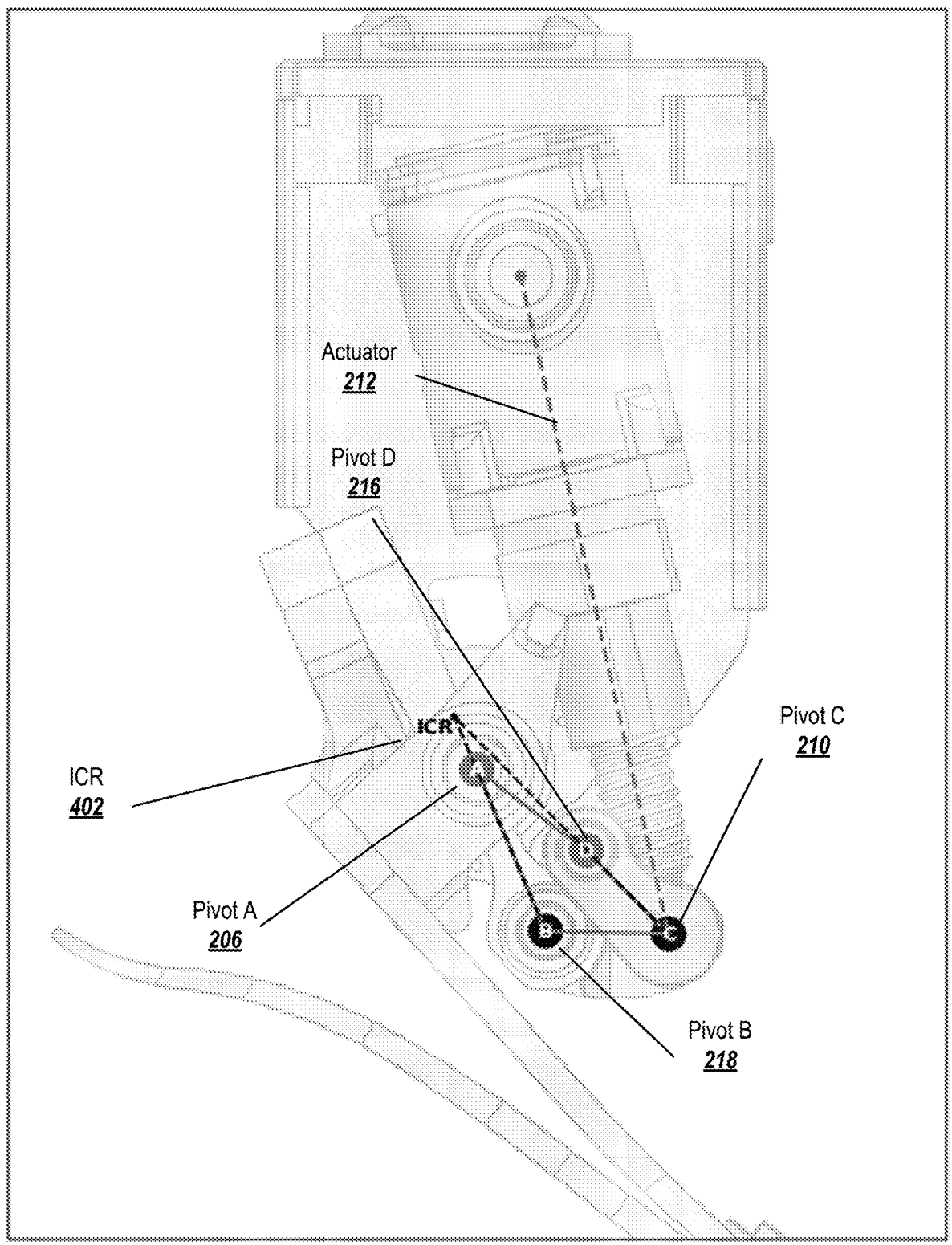
FIG. 4B shows the pivots and links with the foot in a more plantarflexed position than in FIG. 4A.

FIG. 4B shows the linkage in the fully plantarflexed position. The ICR is farther from both pivots C and B, and the relative distances are closer to equal. The resulting advantage at the end of the motion is slightly above 1:1.

Figure 4C:
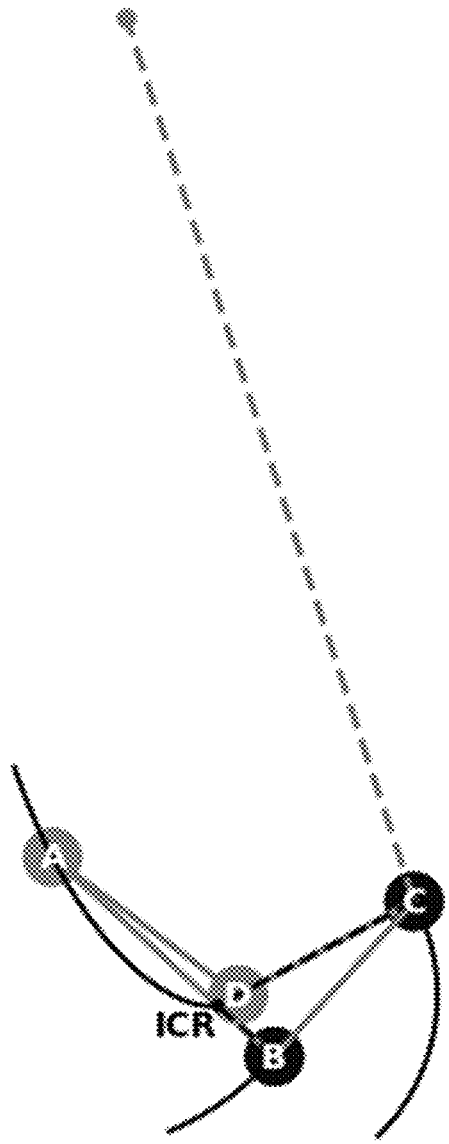
FIG. 4C is a schematic showing respective positions of the pivots and links shown in FIG. 4A at a time when the system is providing a relatively high mechanical advantage.

FIG. 4C shows a schematic of the linkage design, with the pivots and the ICR depicted at the fully dorsiflexed position and curves showing their paths to the fully plantarflexed position. As in FIGS. 4A and 4B, the gray lines represent the links between pivots, and the dotted gray line represents the axis of a linear actuator (e.g. a motor-driven ball screw). This style of schematic will be used throughout this document to depict linkage designs.

Figure 5A:
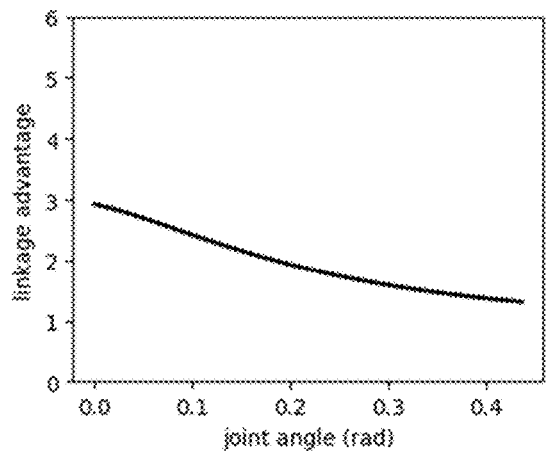
FIGS. 5A-D show the mechanical advantage of the linkage, the overall mechanical advantage of the actuator and linkage, the joint torque provided by the linkage, and the motor torque as a function of ankle joint angle according to the first embodiment.

The mechanical advantage from link BC is plotted against the joint angle in FIG. 5A. The relatively high ratio at the dorsiflexed position is appropriate for high torque operation in that position. The relatively low ratio at the plantarflexed position is appropriate for low torque operation in that position.

The total mechanical advantage from the joint to the actuator, or to the motor within the actuator, would also take into account the relationship of the full actuator force to Fc_cir, the ball screw pitch, the distance La_b, etc. Since the ratio of the full actuator force to Fc_cir depends on the orientation of the actuator to the linkage, it also varies with position.

Figure 5B:
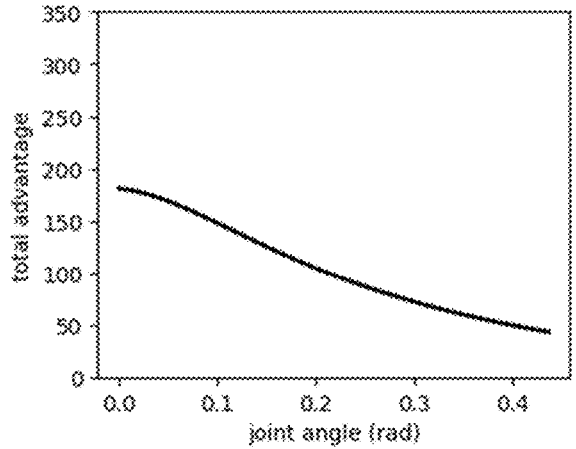

FIG. 5A shows the variation of the linkage advantage versus joint position. As described above, the advantage varies from approximately 3:1 at the dorsiflexed position to just over 1:1 at the plantarflexed position. FIG. 5B shows the total mechanical advantage from the joint to the motor, plotted against joint position.

Figure 5C:
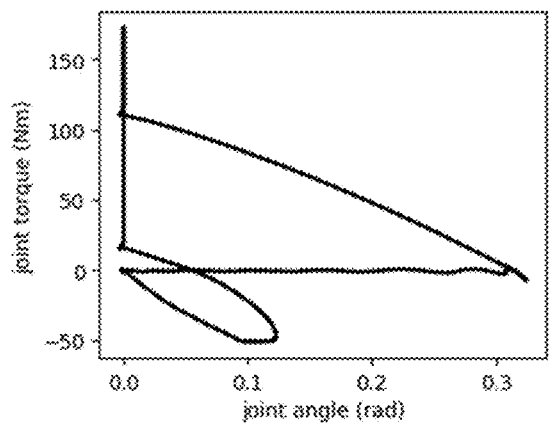
Figure 5D:
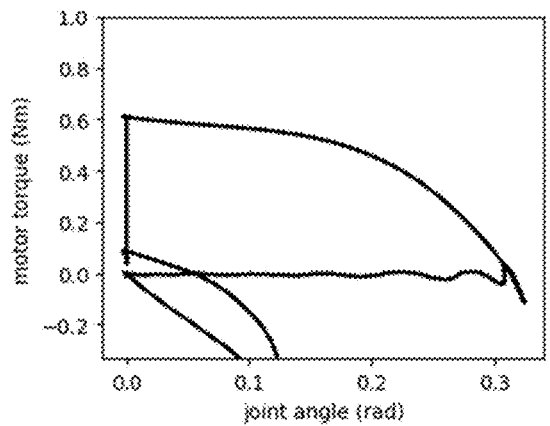

FIG. 5C shows the torque output at the joint of the exemplary embodiment during a typical walking step, plotted against joint position. The highest torques occur at the dorsiflexed position, and the torques in the plantarflexed position are significantly lower. FIG. 5D shows the motor torque plotted against joint position. Due to the variable advantage, the motor torque curve has a different form shape than the joint torque curve.

This definition of the input and output of the four-bar linkage transmission (Fc_cir and Fb_cir, respectively) is convenient for describing the depicted embodiment, but is not generally applicable to all embodiments, in which the actuator may be rotary or linear, and may act on different locations on the linkage. However, all embodiments will share the feature that the kinematics of the linkage provide a variable transmission ratio.

Returning to FIG. 3D, link AB (the foot structure) includes a deformable cantilevered member supporting pivot B that is stiff enough to be considered rigid when calculating the linkage kinematics, but which has sufficient elasticity to allow for the output load of the linkage to be measured with strain gauges. In another embodiment, link AB has greater elasticity, which allows for the linkage output load to be calculated from the deflection (rather than strain) of the member. The deflection is calculated from the relative positions of encoders at pivot A (the joint) and on the motor in the actuator.

In the depicted embodiment, limit stops 207 constrain the motion of the joint and the linkage. A plantarflexion stop between the foot structure and the shank structure prevents over-extension in the position shown in FIG. 3C. In the dorsiflexed position shown in FIG. 3A, a limit stop between link CD and the shank structure prevents over-retraction of the actuator. A secondary dorsiflexion stop between the foot structure and shank structure allows for slightly more joint motion than the stop on the linkage. This secondary dorsiflexion stop allows for deflection in embodiments with an elastic link AB, as described above, and provides a back stop to prevent excessive deflection.

In the depicted embodiment, rotary encoders are disposed at the ankle joint and on the motor in the actuator. Because the kinematics of the linkage are known, the motor encoder can be used to calculate the position of the linkage and the ankle joint. Similarly, the ankle joint encoder can be used to calculate the position of the linkage and motor. From either encoder, since the linkage position is known, the mechanical advantage of the linkage and the over-all transmission ratio from the motor to the joint can be calculated, or pre-calculated, stored, and retrieved for use in the controller. In particular, in the depicted embodiment, the over-all transmission ratio is used to calculate the motor torque required to exert a desired torque at the joint.

In configurations of the depicted embodiment using an elastic link AB for load measurement, the motor and joint encoders are used in tandem to calculate the deflection of the elastic link. The deflection is then used to estimate the load carried by the linkage, based on a known spring rate of the elastic member.

In addition to the exemplary embodiments described above, further embodiments have been contemplated. The four-bar linkage transmission described herein may be applied to a powered prosthesis, orthosis, exoskeleton, or other human augmentation device. It may also be applied to any anatomical joint: ankle, knee, hip, elbow, etc.

The depicted linkages are designed to place positions of high and low advantage optimally for a typical step. In an ankle joint during level ground walking, high torques are generally required when the ankle is fully dorsiflexed, whereas low torque but high speed is generally needed when the ankle is fully plantarflexed. Depending on the application (and the needs for respective high-torque or high-speed regions throughout the operation of the motor), the geometry of the linkage can be modified to best suit the requirements. Linkage configurations can be made to shape the variable transmission ratio is many different ways, to suit different uses.

Figure 6A:
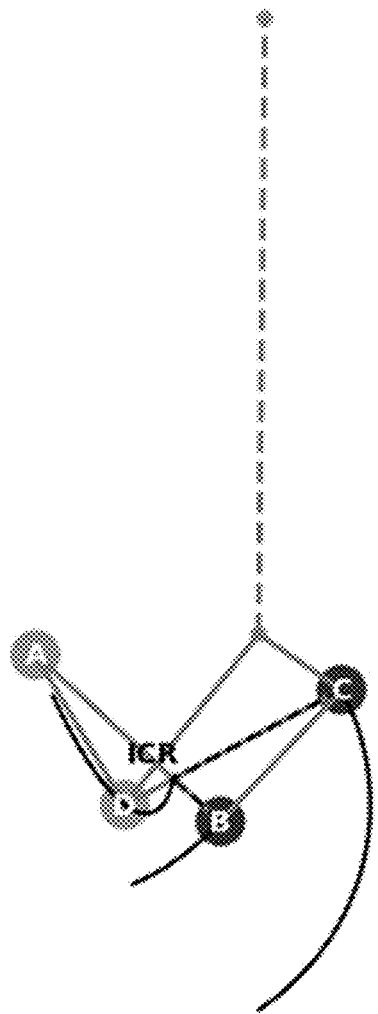
FIGS. 6A-6C show the schematic and advantage plots for a design with the peak mechanical advantage in the middle of the range of motion.
Figure 6B:
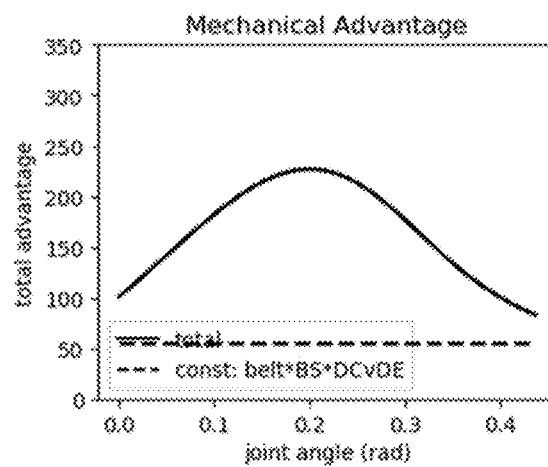
Figure 6C:
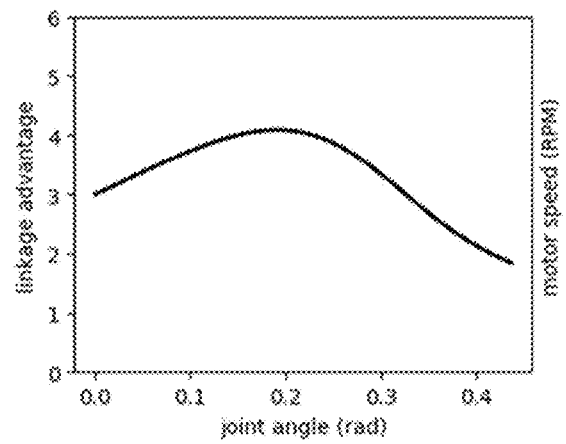
Figure 6D:
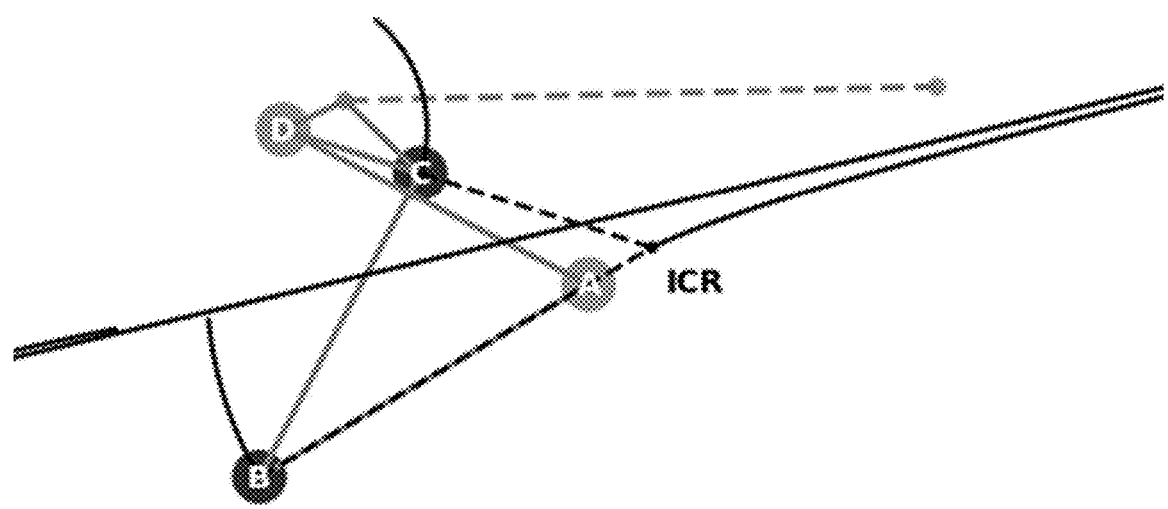
FIGS. 6D-6F show the schematic and advantage plots for a design with the peak mechanical advantage at the fully plantarflexed position.
Figure 6E:
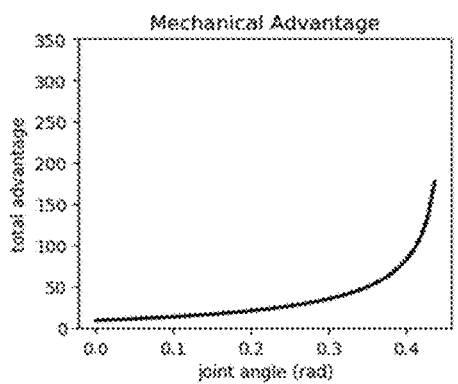
Figure 6F:
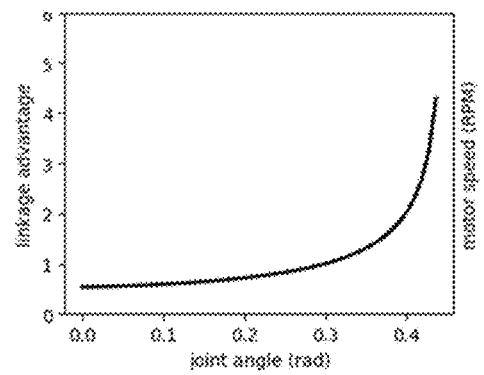

FIGS. 6A-6C show the schematic and advantage plots for a design with the peak mechanical advantage in the middle of the range of motion. FIGS. 6D-6F show the schematic and advantage plots for a design with the peak mechanical advantage at the fully plantarflexed position.

In some alternate embodiments, the linkage may be flipped such that Link AB represents the proximal member (the shank in the case of an ankle) and link AD represents the distal member (the foot in the case of an ankle). The linkage may also be differently configured for bulk or packaging considerations.

Figure 7A:
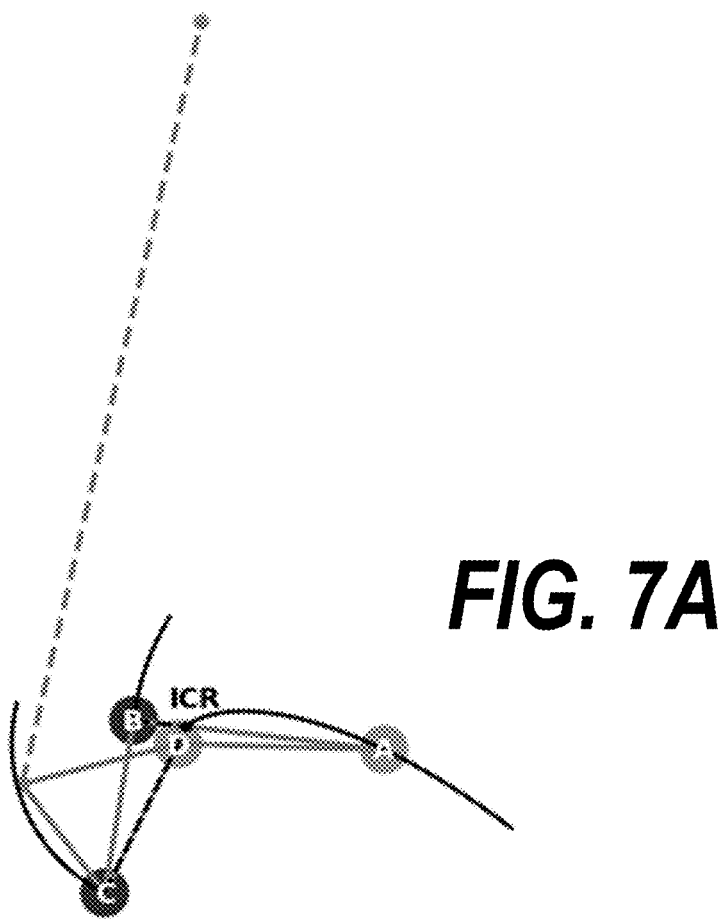
FIG. 7A shows a layout for a linkage similar to the exemplary embodiment, but placed to the rear of the ankle joint.
Figure 7B:
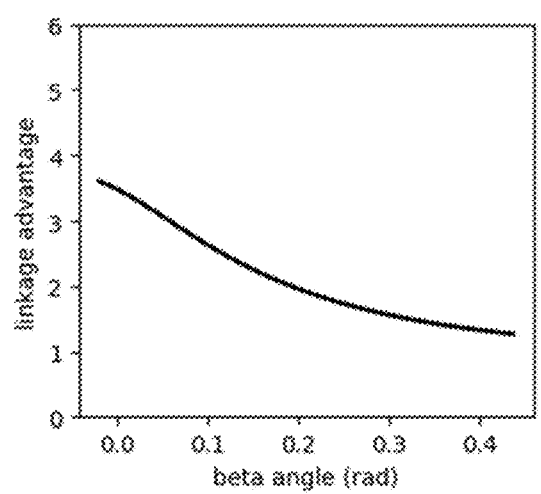
FIG. 7B shows the linkage advantage for the embodiment depicted in FIG. 7A.
Figure 7C:
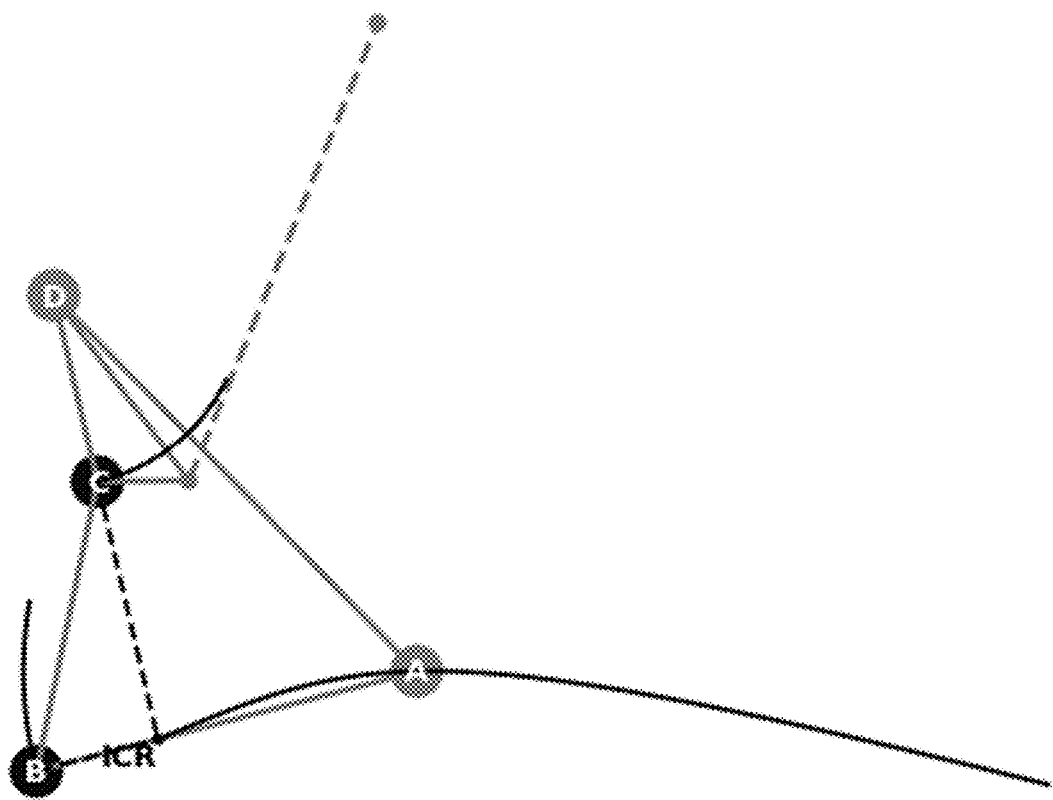
FIGS. 7C and D show a layout and corresponding linkage advantage for another alternate design that places the linkage to the rear of the joint.
Figure 7D:
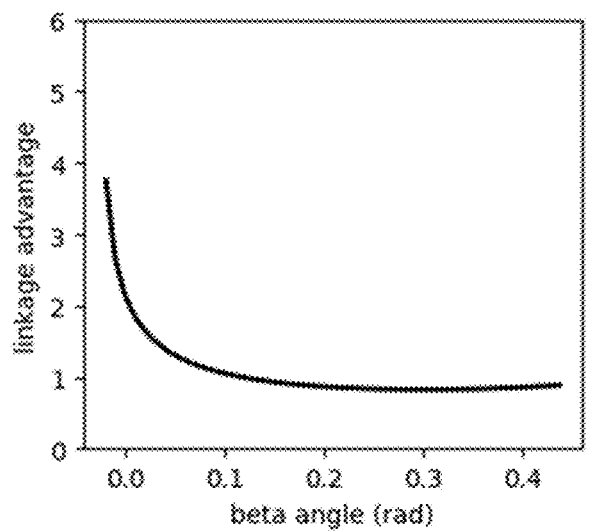

FIG. 7A shows a layout for a linkage similar to the exemplary embodiment, but placed to the rear of the ankle joint. FIG. 7B shows the corresponding linkage advantage. FIGS. 7C and D show a layout and corresponding linkage advantage for another alternate design that places the linkage to the rear of the joint.

The method of actuation may also vary. For instance, the actuator may be anchored to the distal joint structure rather than the proximal joint structure, or to the links BC or CD, or elsewhere in the device. Moreover, the actuator may push, pull, or exert torque on any of the links, or any of pivots B, C, or D. The actuator may also be a rotary actuator, instead of a linear actuator. The actuator may be powered by a motor such as a rotary or linear electric motor, or may be hydraulic, pneumatic, etc.

Figure 8A:
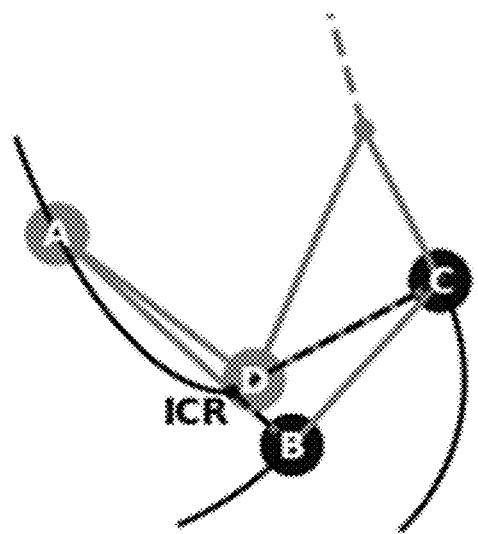
FIG. 8A-C depict a layout and corresponding linkage and total advantages for a design with the actuator pivot not coaxial with pivot C.
Figure 8B:
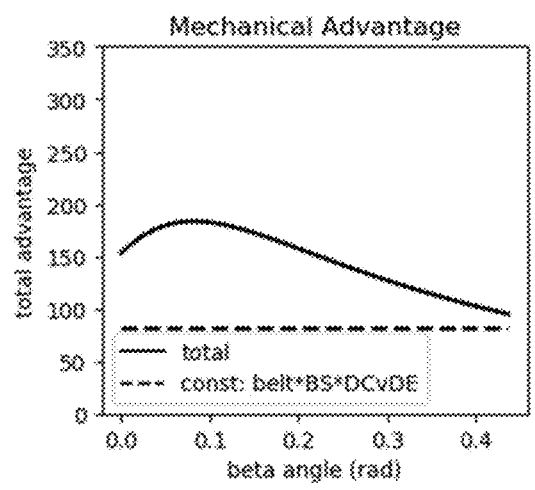
Figure 8C:
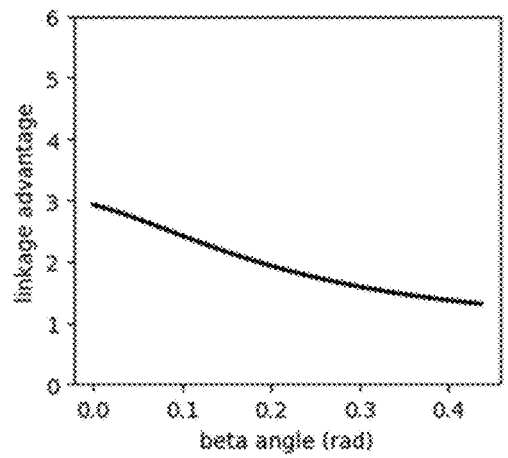

In particular, although in the first embodiment the lower pivot of the actuator is coaxial with pivot C of the linkage, this co-location is not necessary. The actuator may attach anywhere on the linkage, with correspondingly different effects on the transmission ratio. FIG. 8A-C show a layout and corresponding linkage and total advantages for such a design, with the actuator pivot not coaxial with pivot C. The pivot is on link DC in this case.

In the depicted embodiments, the members of the four-bar linkage are nominally rigid with respect to the linkage kinematics so that the linkage position is determined by the ankle joint angle. For example, if the ankle is plantarflexed to 10 degrees, the linkage advantage has a known value that is set and not adjusted during operation of the device. In other embodiments, one or more of the links may be elastic members, which may provide the compliance for a series-elastic actuator. Such elasticity may be useful for shock attenuation, load measurement, or energy storage and may allow a motor to operate in a more efficient torque or rpm range or at lower power by allowing energy storage in elastic elements to occur over a relatively long period of time and then be released quickly. Elasticity in the linkage may make the length or position of one or more links vary under load, making the mechanical advantage dependent on load as well as on position of the actuator or joint. Load dependency could be used, for example, to adjust the characteristics of the varying mechanical advantage to suit different user weights or activity types (e.g. stair ascent versus level ground walking). A spring constant of 300 to 2,000 Nm/radian acting on the pivot point replicating a human joint may be preferred for energy storage.

Moreover, embodiments with non-rigid components separate from the four-bar linkage are also contemplated. For instance, link AB could be elastically joined to a separate structure associated with the anatomical body part (e.g. a foot structure), which would have the benefits of a series elastic actuator as described above. Alternately, an elastic member could be disposed between either end of the actuator and the linkage or other support structures, with similar series elastic benefits.

Adding elastic elements within or external to the linkage may have the effect of changing the linkage positions at which relatively high or low mechanical advantage are desirable. For example, in a foot-ankle prosthesis an elastic link AB is contemplated with sufficient elasticity to be considered non-rigid with respect to the linkage kinematics. In such an embodiment, the linkage position at peak joint torque may move towards the middle or the plantarflexed end of the linkage's range of motion due to deflection under load. In that case, it may be desirable for the mechanical advantage to have a maximum in the middle or plantarflexed end of the linkage range of motion, which can be easily accomplished by one of ordinary skill in the art based on the above disclosure.

In the first embodiment, one or more hardware sensors such as encoders are disposed at the ankle joint and the motor. Alternate embodiments are contemplated that use only the motor encoder, or that use any combination of one or more encoders disposed at the linkage pivots or the motor. In a configuration without significant elasticity, a single encoder at any location on the linkage or actuator could be used to calculate the linkage position and mechanical advantage, and the over-all transmission ratio. In a configuration with elasticity, encoders at any two locations on the linkage and actuator with one encoder on each side of the elastic member(s) could be used to calculate the linkage position and mechanical advantage, the over-all transmission ratio, and the deflection of the elastic member(s) in order to determine the load on the linkage.

Alternate position-measurement hardware sensors could be used in place of encoders for determining the position of a part of the device. For example, linear encoders or proximity sensors, such as a Hall effect sensor, could be used instead of the rotary encoders in the depicted embodiment.

Alternate embodiments are also contemplated in which a kinematic singularity (or self-locking position) of the linkage is used as either a limit stop or a bi-directional lock on the linkage motion.

Figure 9A:
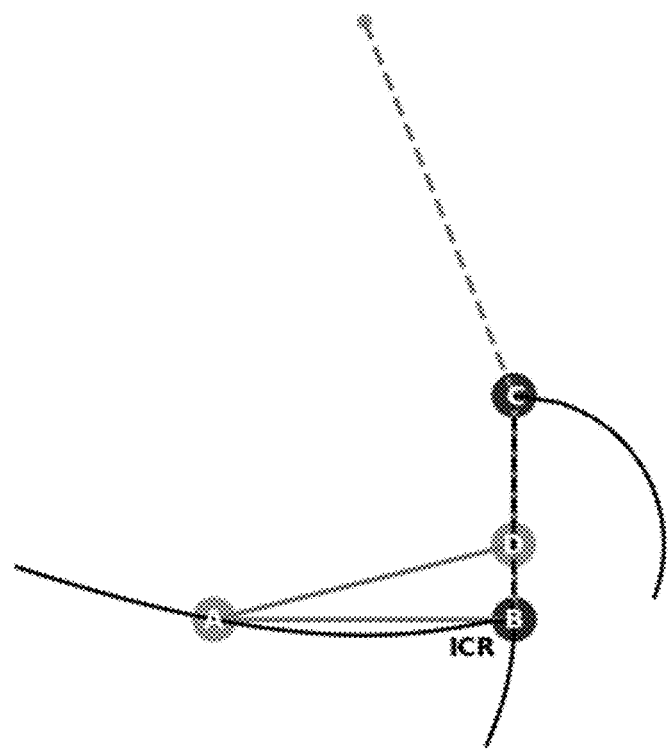
FIGS. 9A-C show a schematic and corresponding advantages for a design that employs a kinematic singularity as a limit stop.
Figure 9B:
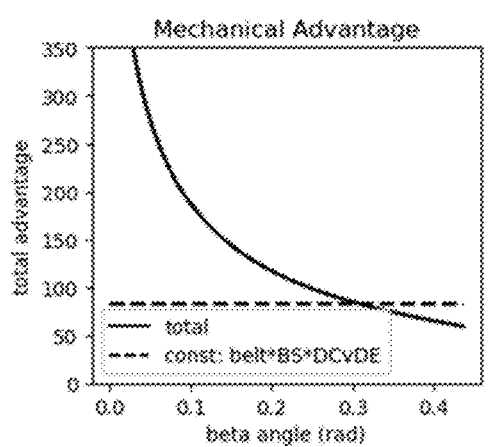
Figure 9C:
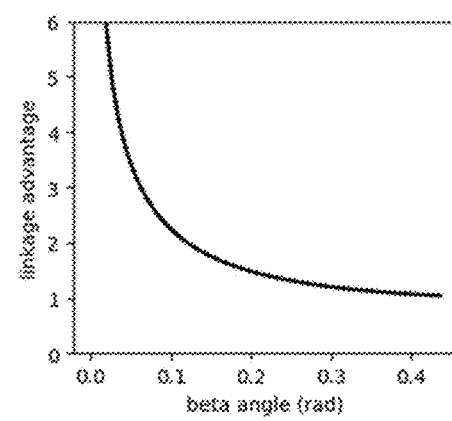

FIGS. 9A-C show a schematic and corresponding advantages for a design that employs a kinematic singularity as a limit stop. In the fully dorsiflexed position shown, a dorsiflexion torque applied to the foot cannot further dorsiflex because the linkage is kinematically locked. The mechanical advantage in this position is effectively infinite.

The components and features of the devices described above may be implemented using any combination of discrete circuitry, application specific integrated circuits (ASICs), logic gates and/or single chip architectures. Further, the features of the devices may be implemented using microcontrollers, programmable logic arrays and/or microprocessors or any combination of the foregoing where suitably appropriate. It is noted that hardware, firmware and/or software elements may be collectively or individually referred to herein as "logic" or "circuit."

It will be appreciated that the exemplary devices shown in the block diagrams described above may represent one functionally descriptive example of many potential implementations. Accordingly, division, omission or inclusion of block functions depicted in the accompanying figures does not infer that the hardware components, circuits, software and/or elements for implementing these functions would be necessarily be divided, omitted, or included in embodiments.

At least one computer-readable storage medium may include instructions that, when executed, cause a system to perform any of the computer-implemented methods described herein.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Moreover, unless otherwise noted the features described above are recognized to be usable together in any combination. Thus, any features discussed separately may be employed in combination with each other unless it is noted that the features are incompatible with each other.

With general reference to notations and nomenclature used herein, the detailed descriptions herein may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein, which form part of one or more embodiments. Rather, the operations are machine operations. Useful machines for performing operations of various embodiments include general purpose digital computers or similar devices.

Some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Various embodiments also relate to apparatus or systems for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove convenient to construct more specialized apparatus to perform the required method steps. The required structure for a variety of these machines will appear from the description given.

It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible. Accordingly, the novel architecture is intended to embrace all such alterations, modifications and variations that fall within the spirit and scope of the appended claims.

The invention claimed is:

1. A human augmentation device comprising:
   a proximal member and a distal member directly connected by a single rotational axis corresponding to a human joint;
   a linkage which transmits force between the proximal and distal members comprising at least four pivot axes and four links respectively connecting the pivot axes (A, B, C, and D), wherein a first link (AB) corresponds to the distal member, a second link (AD) corresponds to the proximal member, third (CD) and fourth (BC) links connect to the first and second links, and the pivot axis (A) connecting the first link and second link is the single rotational axis corresponding to the human joint; and
   an actuator, wherein the linkage and actuator produce a mechanical advantage for the actuator to rotate the distal member relative to the proximal member and the mechanical advantage varies throughout a movement cycle of the linkage as a function of an angle between the proximal and distal members;
   a predefined high-torque range is defined for a portion of the movement cycle during which the actuator imparts a relatively high torque between the proximal and distal members as compared to other portions of the movement cycle; and
   an instantaneous center of rotation (ICR) is defined as a point where lines extending from the first and third links intersect, and the links of the linkage are sized and configured relative to each other to position the ICR relatively farther from a selected pivot of the fourth link as compared to a second pivot of the fourth link when the human augmentation device is in the predefined high-torque range as compared to the other portions of the movement cycle to increase the varying mechanical advantage in the high-torque range.

2. The device of claim 1, wherein the varying mechanical advantage varies by at least a factor of 1.25 throughout an allowed range of motion of the proximal member relative to the distal member.

3. The device of claim 2, where in the distal member is a prosthetic component.

4. The device of claim 1, wherein the proximal and distal members each correspond with a segment of a human limb.

5. The device of claim 1, wherein a torque created by the actuator acts between the proximal and distal members and is a function of at least a rotational position of the proximal member relative to the distal member.

6. The device of claim 1, further comprising
   an encoder configured to generate an output from which a position of the linkage can be determined; and
   a controller configured to:
      determine the position of the linkage from the encoder output,
      use the position of the linkage to transform a desired torque, position, or speed at a rotational axis corresponding to the joint to a target torque, position, or speed of the actuator, and
      control the actuator to apply the target actuator torque, position, or speed.

7. The device of claim 1, wherein the actuator comprises motor having a torque constant selected based on the varying mechanical advantage so as to tune the motor to a limited operating range defined by the varying mechanical advantage.

8. The device of claim 1, wherein the actuator comprises a motor having a speed constant selected based on the varying mechanical advantage so as to tune the motor to a limited operating range defined by the varying mechanical advantage.

9. The device of claim 1, wherein the device is a prosthetic foot-ankle.

10. The device of claim 9, wherein the prosthetic foot-ankle is in a fully dorsiflexed position during at least a part of the predefined high-torque range.

11. The device of claim 1, further comprising a position measuring sensor configured to determine the angle between the proximal and distal members.

12. The device of claim 1, wherein at least one of the links comprises an elastic member.

13. The device of claim 1, wherein the device is a powered human ankle prosthesis, the distal member is a foot member, and the proximal member is a shank member.

14. The device of claim 1, further comprising:
   a joint at the single rotational axis;
   a hardware sensor configured to generate an output from which a position of the linkage can be determined; and
   a controller configured to:
      access the output of the measurement device,
      calculate or retrieve an instantaneous mechanical advantage of the device from an actuator to the joint, and
      control the actuator based in part on the mechanical advantage to apply a target torque or speed to the joint.

15. The device of cl aim 14, wherein:
   a first distance A is defined from a first end of the fourth link to the ICR, and a second distance B is defined from a second end of the fourth link to the ICR; and the linkage is configured to vary the mechanical advantage of the linkage over the movement cycle based at least in part on the first distance A and the second distance B.

16. A method comprising:

providing the human augmentation device of claim 1, and rotating the distal member relative to the proximal member to produce the varying mechanical advantage.

17. The method of claim 16, further comprising determining a position of the linkage, using the position of the linkage to transform a desired torque, position, or speed at the rotational axis corresponding to the joint to a target torque, position, or speed of the actuator, and controlling the actuator to apply the target actuator torque, position, or speed.

18. The method of claim 16, further comprising:

calculating or retrieving an instantaneous mechanical advantage of the device from an actuator to the axis corresponding to the joint, and controlling the actuator based in part on the mechanical advantage to apply a target torque or speed to the joint.

19. The device of claim 1, wherein the proximal and distal members are connected to adjacent links of the four links of the linkage.

* * * * *